United States Patent [19]

Isogai et al.

[11] Patent Number: 4,605,796

[45] Date of Patent: Aug. 12, 1986

[54] PROCESS FOR PRODUCING ETHANOL

[75] Inventors: Nobuo Isogai; Takashi Okawa; Motoyuki Hosokawa; Toshiyasu Watanabe; Natsuko Wakui, all of Niigata, Japan

[73] Assignee: Agency of Industrial Science and Technology, Tokyo, Japan

[21] Appl. No.: 682,335

[22] Filed: Dec. 17, 1984

[30] Foreign Application Priority Data

Dec. 26, 1983 [JP] Japan ................................ 58-244172

[51] Int. Cl.$^4$ ........................ C07C 29/00; C07C 31/08
[52] U.S. Cl. .................................... 568/902; 560/265; 568/671
[58] Field of Search ......................................... 568/902

[56] References Cited

U.S. PATENT DOCUMENTS

| 3,248,432 | 4/1966 | Riley et al. | 568/902 |
|---|---|---|---|
| 3,285,948 | 11/1966 | Butler | 568/902 |
| 4,133,966 | 1/1979 | Pretzer et al. | 568/902 |
| 4,205,190 | 5/1980 | Gane et al. | 568/902 |
| 4,233,466 | 11/1980 | Fiato | 568/902 |
| 4,262,154 | 4/1981 | Gane et al. | 568/902 |
| 4,304,946 | 12/1981 | Isogai et al. | 568/902 |
| 4,319,056 | 3/1982 | Gane et al. | 568/902 |
| 4,328,375 | 5/1982 | Barlow | 568/902 |
| 4,339,608 | 7/1982 | Pretzer et al. | 568/902 |
| 4,346,020 | 8/1982 | Pretzer et al. | 568/902 |
| 4,348,541 | 9/1982 | Doyle | 568/902 |
| 4,352,947 | 10/1982 | Habib et al. | 568/902 |
| 4,355,192 | 10/1982 | Cornils et al. | 568/902 |
| 4,409,404 | 10/1983 | Pretzer et al. | 568/902 |
| 4,424,383 | 1/1984 | Cornils et al. | 568/902 |
| 4,438,020 | 3/1984 | Habib et al. | 568/902 |
| 4,454,358 | 6/1984 | Kummer et al. | 568/902 |
| 4,472,526 | 9/1984 | Cornils et al. | 568/902 |
| 4,476,326 | 10/1984 | Lin | 568/902 |

FOREIGN PATENT DOCUMENTS

| 1546428 | 5/1979 | United Kingdom . | |
|---|---|---|---|
| 2036739 | 7/1980 | United Kingdom | 568/902 |
| 2082181 | 3/1982 | United Kingdom | 568/902 |
| 2088870 | 6/1982 | United Kingdom | 568/902 |

*Primary Examiner*—J. E. Evans
*Attorney, Agent, or Firm*—Browdy and Neimark

[57] ABSTRACT

A process for producing ethanol which comprises reacting methanol, carbon monoxide and hydrogen in the presence of (a) a catalyst comprising cobalt or a cobalt compound and a tertiary phosphine as an effective component and (b) promoter comprising an aromatic carboxylic acid, an ester thereof, or a cobalt salt of aromatic carboxylic acid is disclosed. According to the present invention, formation of by-products becomes less and selectivity to realizable ethanol becomes higher.

9 Claims, No Drawings

PROCESS FOR PRODUCING ETHANOL

BACKGROUND OF THE INVENTION

This invention relates to a process for producing ethanol from methanol, carbon monoxide and hydrogen selectively.

It was known in the prior art that ethanol was produced from methanol, carbon monoxide and hydrogen by using a catalyst comprising a cobalt component and an iodine or bromine component and optionally a ruthenium component, an osmium component and a ligand. For example, Japanese Patent Publication (kokoku) No. 24863/1963 discloses a process for producing ethanol which comprises reacting methanol, carbon monoxide and hydrogen in the presence of a cobalt catalyst and an iodine co-catalyst. U.S. Pat. No. 3,285,948 discloses a process for producing ethanol which comprises reacting methanol, carbon monoxide and hydrogen in the presence of a catalyst comprising a soluble cobalt compound, iodine or an iodine compound and a ruthenium compound.

Japanese Patent Publication (kokai) No. 147009/1978 discloses a process for producing ethanol which comprises reacting methanol, carbon monoxide and hydrogen in the presence of a cobalt catalyst, an iodine or bromine and an organic phosphorus compound co-catalyst and a large amount of monocarboxylic acid or derivatives thereof. However, such monocarboxylic acid or derivatives thereof forms an ester with the ethanol produced by the reaction or the methanol which is a starting material; and the use of large amount of such acid lowers the selectivity to neat ethanol. Moreover, the resulting complex composition of the reaction mixture makes the recovering process for ethanol complicated.

Recently, it has been proposed to add a variety of ligands, such as tertiary phosphine, tertiary arsines or tertiary antimony to the prior catalyst for producing ethanol from methanol, carbon monoxide and hydrogen. For example, British Pat. No. 1,546,428 discloses a process for producing ethanol by reacting methanol, carbon monoxide and hydrogen in a hydrocarbon solvent in the presence of the catalyst composed of cobalt-halide-tertiary phosphine.

Japanese Patent Publication (kokai) No. 49326/1980 discloses a multidentate ligand containing cobalt-bromine or iodine-nitrogen or phosphorus atom as such catalyst.

British Pat. No. 2,036,739 discloses a process for producing ethanol by reacting methanol, carbon monoxide and hydrogen in the presence of a catalyst composed of cobalt and a metal of Group VIII of the Periodic Table (Fe, Ru, Os, Rh, Ir, Ni, Pd and Pt), promoter composed of a tertiary phosphine, a tertiary arsine or a tertiary antimony and iodide or bromine.

Japanese Patent Publication (kokai) No. 92330/1980 discloses a catalyst comprising hydride cobalt carbonyl complex, iodine, a ruthenium compound and a tertiary phosphine, a tertiary antimony or a tertiary arsine as such catalyst. U.S. Pat. No. 4,233,466 discloses a catalyst for production of ethanol from methanol, carbon monoxide and hydrogen which comprises cobalt, ruthenium, iodine and a tertiary phosphine in which a molar ratio of phosphorus to iodine is between 1:0.36–1:5 and a molar ratio of phosphorus to cobalt is more than 1.5.

However, when methanol is reacted with carbon monoxide and hydrogen in the presence of any one of these known catalysts, by-products, such as dimethyl ether, methyl ethyl ether, diethyl ether, acetaldehyde, dimethoxy ethane, acetic acid, methyl formate, methyl acetate, ethyl acetate and other compounds of $C_2$ or more other than ethanol (object product) are formed, so selectivity to neat ethanol is low.

On the other hand, Japanese Patent Publication (kokoku) No. 24863/1963 or U.S. Pat. No. 3,285,948 discloses a process for producing ethanol which comprises reacting methanol, carbon monoxide and hydrogen at a temperature of 175°–230° C. and a pressure of more than 281 Kg/cm$^2$G in the presence of a catalyst comprising cobalt-iodine or a catalyst comprising cobalt-iodine-ruthenium and in the absence of any solvent. Since the catalysts do not contain any ligands, it is easy to handle them. However, when the above catalysts are used, by-products, such as ethers and methyl acetate are formed in a large amount, so selectivity to neat ethanol becomes lower extremely.

When a catalysts comprising cobalt-iodine or cobalt-iodine-ruthenium and a ligand are used, formation of by-product, such as ethers are suppressed. However, since the catalysts contain ligands, activity of the catalysts is lowered. Therefore, in case of using catalysts containing ligands, the reaction must be carried out at a higher temperature. This results in forming by-products and lowering selectivity to ethanol. Particularly, the catalysts contain cobalt and ruthenium as well as iodine or bromine and ligands, such as a tertiary phosphine, a tertiary antimony or a tertiary arsine as a ligand, so the following shortcomings are produced in case of carrying out the reaction in the presence of the catalyst on a commercial base:

Since ligands, such as a tertiary phosphine are instable to heat, the ligands are likely to be decomposed in the reaction system, or quality of the ligands is likely to be changed. Therefore, it is difficult to recover the active catalysts from the system. In addition, recovery of each component constituting the catalysts not only need complicated operation, but also loss of the catalysts is great in recovery of the catalysts. Since the catalysts are costly, loss of the catalysts is unpreferablly in case of recovering the catalysts.

In the prior processes, there were problems in respect of selectivity to ethanol, reaction speed and recovery of the catalyst. The prior processes are not industrially satisfactory.

SUMMARY OF THE INVENTION

The present inventors carried out research for overcoming the shortcomings mentioned above. As a result, we found that when methanol reacts with carbon monoxide and hydrogen in the presence of (a) a catalyst containing a cobalt component and a tertiary phosphine and (b) small amount of a promoter comprising an aromatic carboxylic acid, an ester thereof or a cobalt salt of aromatic carboxylic acid, ethanol is produced in high selectivity to ethanol and in high reaction rate.

This invention relates to a process for producing ethanol which comprises reacting methanol, carbon monoxide and hydrogen in the presence of (a) a catalyst comprising cobalt or a cobalt compound and a tertiary phosphine as an effective component and (b) a promoter comprising an aromatic carboxylic acid, an ester thereof, or a cobalt salt of aromatic carboxylic acid.

DETAILED DESCRIPTION OF THE INVENTION

The cobalt compounds employed in the practice of this invention include, for example, cobalt carbonyls, such as dicobalt octacarbonyl and cobalt hydride tetracarbonyl, an inorganic cobalt compound, such as cobalt hydroxide, cobalt carbonate or basic cobalt carbonate, an organic cobalt compound, such as a cobalt organic acid salt, cobaltocene or cobalt acetyl acetonate, or other cobalt compounds which produce cobalt carbonyl in the reaction system. The cobalt compound may be used alone or as a mixture. Dicobalt octacarbonyl is preferable.

The amount of the cobalt compound employed is in the range of 1–300 mg-atom, preferably 5–100 mg-atom in terms of cobalt per 1 mol of methanol. When the amount of cobalt compound is less than the lower limit mentioned above, though the reaction proceeds, the reaction rate is lowered. The use of cobalt compound in an amount of more than the upper limit merely adds to production cost.

The tertiary phosphines of the present invention include, for example, tri-n-butyl phosphine, triphenyl phosphine, tri-p-tolylphosphine, tricyclohexyl phosphine, bis(1,4-diphenyl phosphino)butane and bis(1,6-diphenyl phosphino)hexane. Tri-n-butyl phosphine is preferable.

The amount of the tertiary phosphine may be employed so that the atomic ratio of cobalt to phosphorus is in the range of 1:0.1 to 1:3, preferably 1:0.5 to 1:2.5. The use of the tertiary phosphine in an amount of less than the lower limit is less effective for suppressing formation of esters or ethers. The use of tertiary phosphine in an amount of more than the upper limit lowers the reaction rate.

The aromatic carboxylic acids employed in the practice of this invention include monocarboxylic acids, such as, for example, benzoic acid, o-toluic acid, m-toluic acid and p-toluic acid; polycarboxylic acids, such as phthalic acid, isophthalic acid, terephthalic acid, trimellitic acid and trimesic acid; or esters or cobalt salts of these acids. The amount of the acid, ester or cobalt salt of the acid employed may be in the range of 0.5–30 milli mol, preferably 1–15 milli mol per 1 mol of methanol. The use of the promoter in an amount of less than the lower limit does not sufficiently promote the reaction. The use of the promoter in an amount of more than the upper limit lowers selectivity to neat ethanol as well as selectivity to realizable ethanol.

When aliphatic acids, such as formic acid, and acetic acid or the esters or cobalt salts thereof are used in place of the promoter, the aliphatic acids do not increase the reaction rate and the selectivity to ethanol.

Use of solvent is not critical in this invention. However, it is preferable that the reaction is carried out in the presence of solvents which do not give a bad effect on the reaction.

The solvents which are inert to the reaction system include hydrocarbons and ethers. Hydrocarbon solvents include, for example, aromatic hydrocarbons, such as toluene, benzene and xylene; aliphatic hydrocarbons, such as hexane and octane; and alicyclic hydrocarbons, such as cyclohexane. The ether solvents include, for example, diethyl ether, diiopropyl ether, dioxane and tetrahydrofuran. Toluene is preferable.

The amount of the solvent employed may be in the range of 0.1–10 mol, preferably 0.2–5 mol per 1 mol of methanol. Use of solvent in an amount of more than the above upper limit lowers the space time yield of ethanol and is not practical.

The reaction temperature depends on the catalyst employed and other reaction conditions. In general, the temperature may be in the range of 150°–300° C., preferably 200°–260° C. Though the reaction proceeds at a temperature below 150° C., the reaction rate is low; at temperature above 300° C. by-products forms.

The reaction pressure may be in the range of more than 50 Kg/cm$^2$, and preferably, the pressure is in the range of 100–500 Kg/cm$^2$ in the practice of the present invention. Carbon monoxide and hydrogen may be used in an amount of more than the stoichiometric amount of methanol. The molar ratio of CO to H$_2$ employed may be in the range of 4:1 to 1:4, preferably 2:1 to 1:3.

Carbon monoxide and hydrogen employed in the present invention may contain argon, nitrogen, carbon dioxide, methane, ethane and other inert gases. In this case, the total partial pressure of each of carbon monoxide and hydrogen is within the above reaction pressure.

The present invention can be carried out either as batch process or as a continuous process.

The present invention is further illustrated by non-limiting Examples and Control tests.

In the following Examples and Control tests, reactivity of methanol, selectivity to ethanol, substantial reactivity of methanol and selectivity to realizable ethanol are expressed by the following equations:

$$\text{Reactivity of methanol (\%)} = \frac{\text{mol of CH}_3\text{OH fed} - \text{mol of unreacted CH}_3\text{OH}}{\text{mol of CH}_3\text{OH fed}} \times 100$$

$$\text{Selectivity to each product (\%)} = \frac{\text{mol of CH}_3\text{OH converted to each product}}{\text{mol of CH}_3\text{OH fed} - \text{mol of unreacted CH}_3\text{OH}} \times 100$$

$$\text{Substantial reactivity of methanol (\%)} = \frac{\text{mol of CH}_3\text{OH fed} - \text{mol of unreacted CH}_3\text{OH} - \text{mol of CH}_3\text{OH converted}^{*1}}{\text{mol of CH}_3\text{OH fed}} \times 100$$

$$\text{Selectivity to realizable ethanol (\%)} = \frac{\text{mol of CH}_3\text{OH converted to realizable C}_2\text{H}_5\text{OH}^{*2}}{\text{mol of CH}_3\text{OH fed} - \text{mol of unreacted CH}_3\text{OH} - \text{mol of CH}_3\text{OH converted}} \times 100$$

*[1] contains components, such as dimethoxy ethane, methyl esters, etc. from which methanol can easily be recovered through hydrolysis
*[2] contains neat ethanol and components, such as acetaldehyde, dimethoxy ethane, ethyl esters, etc., from which ethanol can easily be recovered through hydrogenation or hydrolysis

EXAMPLE 1

Into a shaking type 100 ml autoclave made of stainless steel were charged 10 grams (g) (0.3121 mol) of methanol, 2 g (0.0058 mol) of dicobalt octacarbonyl, 0.20 g (1.64 m mol) of benzoic acid, 3 g (0.0148 mol) of tri-n-butyl phosphine and 10 g (0.109 mol) of toluene. Mixed gas of H$_2$ and CO (molar ratio of 1:1) was fed to pressure of 200 Kg/cm². The reaction was carried out at 225°-230° C. for 1.5 hours.

After the reaction, the autoclave was cooled and the gas remaining inside the autoclave was discharged to atmosspheric pressure. Gas Chromatograph (GC) Analysis (internal standard method) showed reactivity of methanol of 20.9% and selectivity to neat ethanol of 70.7%. Selectivity to each of the following components was as follows:

| | |
|---|---|
| methyl formate | 11.70% |
| methyl ethyl ether | 1.10% |
| methyl acetate | 2.35% |
| acetaldehyde | 0.66% |

This shows substantial reactivity of methanol of 18.1% and selectivity to realizable ethanol of 83.0%.

EXAMPLE 2

The procedures of Example 1 were repeated except that benzoic acid was employed in amounts as shown in Table 1. The results are shown in Table 1.

TABLE 1

| Experiment No. | 1* | 2 | 3 | 4 | 5 | 6 | 7 | 8 |
|---|---|---|---|---|---|---|---|---|
| Amount of benzoic acid employed per 1 mol of CH₃OH (milli mol) | 0 | 1 | 2 | 3 | 5 | 8 | 15 | 20 |
| Selectivity to ethanol (%) | 53.6 | 56 | 63 | 68 | 71 | 70 | 51 | 40 |
| Selectivity to realizable ethanol (%) | 68.1 | 72 | 76 | 80 | 84 | 83 | 74 | 66 |

*The data are the ones of Control Test 1.

It is clear from Table 1 that use of benzoic acid promotes the reaction. Use of benzoic acid in amount of more than 15 milli mol per 1 mol of methanol increases formation of ethyl benzoate and lowers selectivity to neat ethanol and selectivity to realizable ethanol.

EXAMPLES 3-9

The procedures of Example 1 were repeated that the catalysts and promoters were employed in amounts as shown in Table 2. The reaction conditions are also shown in Table 2.

TABLE 2

| Example | 3 | 4 | 5 | 6 | 7 | 8 | 9 |
|---|---|---|---|---|---|---|---|
| methanol g (mol) | 10 (0.3121) | 6 (0.1873) | 10 (0.3121) | 10 (0.3121) | 10 (0.3121) | 10 (0.3121) | 10 (0.3121) |
| Co₂(CO)₈ g (mol) | 2 (0.0058) | 2 (0.0058) | 2 (0.0058) | 2 (0.0058) | 2 (0.0058) | 2 (0.0058) | 2 (0.0058) |
| promoter g (milli mol) | benzoic acid 0.20 (1.64) | benzoic acid 0.20 (1.64) | p-toluic acid 0.22 (1.62) | terephthalic acid 0.27 (1.63) | methyl benzoate 0.22 (1.62) | cobalt benzoate 0.25 (0.83) | benzoic acid 0.30 (2.46) |
| tri-n-butyl phosphine g (mol) | 3 (0.0148) | 3 (0.0148) | 3 (0.0148) | 3 (0.0148) | 3 (0.0148) | 3 (0.0148) | 3 (0.0148) |
| solvent g (mol) | toluene 10 (0.109) | toluene 10 (0.109) | toluene 10 (0.109) | toluene 10 (0.109) | toluene 10 (0.109) | toluene 10 (0.109) | 1,4-dioxane 10 (0.113) |
| reaction temperature °C. | 225-230 | 225-230 | 225-230 | 225-230 | 225-230 | 225-230 | 225-230 |
| reaction time hr | 3.0 | 1.5 | 1.5 | 1.5 | 1.5 | 1.5 | 1.5 |
| reactivity of CH₃OH (substantial reactivity of CH₃OH) | 38.6 (37.0) | 52.3 (51.7) | 22.5 (19.7) | 20.9 (18.8) | 22.4 (19.9) | 24.3 (22.4) | 29.7 (29.2) |
| selectivity to each compound % | | | | | | | |
| ethanol | 76.1 | 70.5 | 71.3 | 71.1 | 74.7 | 71.4 | 72.8 |
| methyl formate | 2.67 | 0.40 | 10.5 | 8.11 | 9.15 | 6.11 | 1.31 |
| methyl acetate | 0.95 | 0.23 | 2.41 | 2.02 | 2.23 | 1.01 | 0.50 |
| methyl ethyl ether | 1.72 | 1.82 | 1.55 | 1.11 | 1.70 | 2.05 | 1.86 |
| acetaldehyde | 0.25 | 0.22 | 0.53 | 0.66 | 0.53 | 0.38 | 0.16 |
| realizable ethanol | 80.6 | 72.6 | 83.0 | 80.4 | 85.7 | 79.0 | 75.2 |

CONTROL TEST 1

The procedure of Example 1 was repeated except that benzoic acid was not employed. The results are shown in the following:

| | |
|---|---|
| reactivity of methanol | 15.0% |
| selectivity to neat ethanol | 53.6% |
| selectivity to methyl formate | 17.8% |
| selectivity to methyl acetate | 1.81% |
| selectivity to methyl ethyl ether | 1.86% |
| selectivity to acetaldehyde | 1.02% |

This shows substantial reactivity of methanol of 12.6% and selectivity to realizable ethanol of 68.1%.

CONTROL TESTS 2-5

The procedures of Example 1 were repeated except that the components were employed in amounts as shown in Table 3.

(i) No promoter is employed in Control Tests 1-2. It is clear from comparison of Examples 1, 3, 5, 6, 7 and 8 and Control Tests 1 and 2 that the promoters enhance the activity of catalyst and selectivity to object product.

(ii) No tertiary phosphine is employed in Control Test 3. It is clear from comparison of Example 1 and Control Test 3 that combination of the cobalt component, the tertiary phosphine and the promoter is effective for reaction of methanol, hydrogen and carbon monoxide.

(iii) Acetic acid is employed in place of the promoter in Control Test 4. It is clear from Control Test 4 that acetic acid (aliphatic carboxylic acid) is not effective for the reaction.

(iv) The tertiary phosphine is not employed and great amount of propionic acid is employed in Control Test 5. In this case, though reactivity of methanol is high, selectivity to neat ethanol and realizable ethanol is low.

TABLE 3

| Control Test No. | 2 | 3 | 4 | 5 |
|---|---|---|---|---|
| methanol g (mol) | 10 (0.3121) | 10 (0.3121) | 10 (0.3121) | 13 (0.4057) |
| Co$_2$(CO)$_8$ g (mol) | 2 (0.0058) | 2 (0.0058) | 2 (0.0058) | cobalt acetate tetrahydrate 1.25 (0.0050) |
| promotor g (milli mol) | — | benzoic acid 0.20 (1.64) | acetic acid 0.10 (1.67) | propionic acid 15 (203) |
| tri-n-butyl phosphine g (mol) | 3 (0.0148) | — | 3 (0.0148) | — |
| solvent g (mol) | toluene 10 (0.109) | toluene 10 (0.109) | toluene 10 (0.109) | — |
| reaction temperature °C. | 225–230 | 225–230 | 225–230 | 180–185 |
| reaction time hr | 3.0 | 1.5 | 1.5 | 8 |
| reactivity of CH$_3$OH (substantial reactivity of CH$_3$OH) % | 28.7 (26.3) | 9.10 (7.11) | 17.9 (17.1) | 67.3 (33.9) |
| reactivity to each compound % | | | | |
| ethanol | 56.3 | 23.4 | 54.8 | 19.5 |
| methyl formate | 7.00 | 18.00 | 2.68 | 0.26 |
| methyl acetate | 0.61 | 1.41 | 0.50 | 8.72 |
| methyl ethyl ether | 2.70 | 6.53 | 2.78 | ethyl propionate 11.3 |
| acetaldehyde | — | — | 0.42 | 0.48 |
| realizable ethanol | 62.9 | 33.8 | 59.0 | 64.5 |

EXAMPLE 10

Into reactor having diameter of 30 millimeter and length of 1.5 meter was continuously charged 837.5 g/hr of feed solution containing 34.9% of methanol, 8.64% of Co$_2$(CO)$_8$, 0.65% of benzoic acid, 13% of tri-n-butyl phosphine and 43.1% of benzene. Raw material gas (CO:H$_2$=1:1) was continuously charged into the reactor in amount of 800 liter/hr. The reaction was effected at 235° C. and 290 Kg/cm$^2$. The reaction solution was discharged from the reactor in amount of 947.1 g/hr. The reaction solution contained 16.2% of methanol, 18.0% of ethanol, 0.3% of acetaldehyde, 0.54% of methyl formate, 0.25% of diethyl ether, 0.1% of methyl acetate and 0.72% of propanol. This corresponds to reactivity of methanol of 47.5% and selectivity to neat ethanol of 85.5%; this shows substantial reactivity of methanol of 46.4% and selectivity of realizable ethanol of 90.5%.

What is claimed is:

1. A process for producing ethanol which comprises reacting methanol, carbon monoxide, and hydrogen in the presence of a catalyst consisting of:
  (a) cobalt or a cobalt compound selected from the group consisting of cobalt carbonyls, dicobalt octacarbonyl, cobalt hydride tetracarbonyl, cobalt hydroxide, cobalt carbonate, basic cobalt carbonate, cobaltocene, and cobalt acetyle acetonate;
  (b) tertiary phosphine selected from the group consisting of tri-n-butyl phosphine, triphenyl phosphine, tri-p-tolylphosphine, tricyclohexyl phosphine; and a promoter consisting of an aromatic acid, or cobalt salt, or ester thereof, selected from the group consisting of benzoic acid, o-toluic acid, m-toluic acid, p-toluic acid, phthalic acid, terephthalic acid, isophthalic acid, trimellitic acid, and trimesic acid.

2. The process as defined in claim 1 wherein the cobalt compound is dicobalt octacarbonyl.

3. The process as defined in claim 1 wherein the promoter is benzoic acid.

4. The process as defined in claim 1 wherein the tertiary phosphine is tri-n-butyl phosphine.

5. The process as defined in claim 1 wherein the reaction is carried out in the presence of a solvent.

6. The process as defined in claim 5 wherein the solvent is toluene.

7. The process as defined in claim 1 wherein carbon monoxide and hydrogen are used in an amount of more than the stoichiometric amount of methanol.

8. The process as defined in claim 1 wherein the reaction pressure is in the range of 50–500 Kg/cm$^2$.

9. The process as defined in claim 1 wherein the reaction temperature is in the range of 150°–300° C.

* * * * *